(12) United States Patent
McMeekin et al.

(10) Patent No.: US 6,957,924 B1
(45) Date of Patent: Oct. 25, 2005

(54) TEXTURED FILM DEVICES

(75) Inventors: Linda McMeekin, Bound Brook, NJ (US); Shmuel Dabi, Highland Park, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 09/503,262

(22) Filed: Feb. 14, 2000

(51) Int. Cl.$^7$ ............................................. A41L 7/02
(52) U.S. Cl. ......................... 401/201; 401/7; 401/261; 442/402; 15/208
(58) Field of Search .................. 401/7, 201, 261, 401/265; 15/104.93, 104.84, 209.1, 208; 428/198; 442/402

(56) References Cited

U.S. PATENT DOCUMENTS

| | | |
|---|---|---|
| 1,351,311 A | 8/1920 | Vimberg |
| 2,102,858 A | 12/1937 | Schlumbohm |
| 2,209,914 A | 7/1940 | Gerber et al. |
| 2,607,940 A | 8/1952 | Miller |
| 2,961,677 A | 11/1960 | Zecchini |
| 2,980,941 A | 4/1961 | Miller |
| 3,054,148 A | 9/1962 | Zimmerli ........................ 18/56 |
| 3,167,805 A | 2/1965 | Zuppinger et al. |
| 3,306,292 A | 2/1967 | Spees |
| 3,324,500 A | 6/1967 | Fuller et al. |
| 3,334,374 A | 8/1967 | Watkins, Jr. |
| 3,334,790 A | 8/1967 | Eaton |
| 3,362,776 A | 1/1968 | Knorr |
| 3,394,211 A | 7/1968 | MacDuff |
| 3,466,131 A | 9/1969 | Arcudi |
| 3,635,567 A | 1/1972 | Richardson, Jr. |
| 3,768,619 A | 10/1973 | Avery |
| 3,826,259 A | 7/1974 | Bailey |
| 3,860,349 A | 1/1975 | Scott |
| 3,870,419 A | 3/1975 | Saga |

(Continued)

FOREIGN PATENT DOCUMENTS

| | | | |
|---|---|---|---|
| CA | 1158008 | | 12/1983 |
| CA | 2007694 | | 7/1990 |
| CA | 2007911 | | 7/1990 |
| CA | 1283515 | | 4/1991 |
| CA | 1323281 | | 10/1993 |
| CA | 2236453 | A * | 5/1997 |
| CA | 2295643 | | 2/1999 |
| CA | 2260435 | | 8/1999 |
| CA | 2010502 | | 12/1999 |
| DE | 3441594 | | 5/1986 |
| EP | 0 032 793 | | 1/1981 |
| EP | 0 170 821 | | 2/1986 |
| EP | 1 170 010 | | 2/1986 |
| EP | 0 252 459 | | 1/1988 |
| EP | 0 266 929 | B1 | 5/1988 |
| EP | 0 388 718 | | 3/1993 |

(Continued)

OTHER PUBLICATIONS

Packaging of Edhen Jabon de Avena manufactured by Eduardo Cardenas Diaz, publicly available prior to Jun. 13, 2001 (photocopy attached).

(Continued)

Primary Examiner—David J. Walczak

(57) ABSTRACT

A textured film device formed from at least one layer of gathered textured film. These devices are capable of producing excellent lather when used with a cleanser and are soft to the touch. Other textured film devices include mitts, gloves, washcloths, and the like formed from at least one layer of textured film.

Also provided are systems comprised of the textured film devices and at least one active material selected from cleansers; moisturizers, conditioners; sunscreens; shaving foams; tanning agents; anti-acne agents; anti-aging agents; anti-irritant agents; perfumes/fragrances; and mixtures thereof.

40 Claims, 14 Drawing Sheets

U.S. PATENT DOCUMENTS

| | | | |
|---|---|---|---|
| 3,929,135 A | 12/1975 | Thompson | |
| 3,977,452 A | 8/1976 | Wright | |
| 3,977,796 A | 8/1976 | Gillespie et al. | |
| 3,989,393 A | 11/1976 | Frumkin et al. | |
| 4,154,542 A | 5/1979 | Rasmason | |
| 4,173,978 A | 11/1979 | Brown | |
| 4,183,684 A | 1/1980 | Avery, Jr. | |
| 4,188,304 A | 2/1980 | Clarke et al. | |
| 4,189,802 A | 2/1980 | Lansbergen | |
| 4,190,550 A | 2/1980 | Campbell | |
| 4,228,834 A | 10/1980 | Desnick | |
| 4,348,293 A | 9/1982 | Clarke et al. | |
| 4,373,224 A | 2/1983 | Bandai et al. | |
| 4,410,441 A | 10/1983 | Davies et al. | |
| 4,436,780 A * | 3/1984 | Hotchkiss et al. | 15/209.1 |
| 4,456,570 A | 6/1984 | Thomas et al. | |
| 4,457,640 A | 7/1984 | Anderson | |
| 4,457,643 A | 7/1984 | Caniglia | |
| 4,469,463 A | 9/1984 | Van Overloop | |
| 4,473,611 A | 9/1984 | Haq | 428/198 |
| 4,478,530 A | 10/1984 | Van Overloop | |
| 4,480,939 A | 11/1984 | Upton | |
| 4,515,703 A | 5/1985 | Haq | |
| 4,525,091 A | 6/1985 | Van Overloop | |
| 4,525,411 A * | 6/1985 | Schmidt | 15/209.1 |
| 4,535,020 A | 8/1985 | Thomas et al. | |
| 4,563,103 A | 1/1986 | Van Overloop et al. | |
| 4,576,737 A | 3/1986 | Johnson | |
| 4,582,625 A | 4/1986 | George | |
| 4,603,069 A | 7/1986 | Haq et al. | 428/76 |
| 4,627,129 A | 12/1986 | Wittes | |
| 4,629,643 A | 12/1986 | Curro et al. | |
| 4,728,006 A | 3/1988 | Drobish et al. | |
| 4,741,877 A | 5/1988 | Mullane, Jr. | |
| 4,759,754 A | 7/1988 | Korpman | |
| 4,772,444 A | 9/1988 | Curro et al. | |
| 4,782,975 A | 11/1988 | Coy | |
| 4,789,262 A | 12/1988 | Sanchez | |
| 4,812,067 A | 3/1989 | Brown et al. | |
| 4,818,421 A | 4/1989 | Boris et al. | |
| 4,820,579 A | 4/1989 | Aszman | |
| 4,839,216 A | 6/1989 | Curro et al. | |
| 4,842,596 A | 6/1989 | Kielpikowski et al. | |
| 4,904,524 A | 2/1990 | Yoh | |
| 4,935,158 A | 6/1990 | Aszman et al. | |
| 4,953,250 A | 9/1990 | Brown | |
| 4,990,144 A | 2/1991 | Blott | |
| 5,022,517 A | 6/1991 | Benitez | |
| 5,024,799 A | 6/1991 | Harp et al. | |
| 5,031,759 A | 7/1991 | Ogilvie | |
| 5,053,270 A | 10/1991 | Mack | |
| 5,079,013 A | 1/1992 | Belanger | |
| 5,090,832 A | 2/1992 | Rivera et al. | |
| 5,098,755 A * | 3/1992 | Tanquary et al. | 428/35.5 |
| 5,144,744 A | 9/1992 | Campagnoli | |
| 5,207,725 A | 5/1993 | Pinketon | |
| 5,238,307 A | 8/1993 | Mooney et al. | |
| 5,242,433 A | 9/1993 | Smith et al. | |
| 5,254,109 A | 10/1993 | Smith et al. | |
| 5,326,685 A | 7/1994 | Gaglio et al. | |
| 5,366,125 A | 11/1994 | Procido | |
| 5,380,110 A | 1/1995 | Festa | |
| 5,409,640 A | 4/1995 | Giret et al. | |
| 5,412,830 A | 5/1995 | Girardot et al. | |
| 5,462,378 A | 10/1995 | Webb | |
| 5,486,064 A | 1/1996 | Schulte | |
| 5,492,646 A | 2/1996 | Langley et al. | |
| 5,498,378 A | 3/1996 | Tsaur et al. | |
| 5,525,397 A * | 6/1996 | Shizuno et al. | 15/209.1 |
| 5,538,732 A | 7/1996 | Smith et al. | |
| 5,545,456 A | 8/1996 | Suida | |
| 5,558,874 A | 9/1996 | Haber et al. | |
| 5,586,732 A | 12/1996 | Yamauchi et al. | |
| 5,620,694 A | 4/1997 | Girardot | |
| 5,632,420 A | 5/1997 | Lohrman et al. | |
| 5,650,384 A | 7/1997 | Gordon et al. | |
| 5,651,455 A | 7/1997 | Garcia | |
| 5,680,969 A | 10/1997 | Gross | |
| 5,681,574 A | 10/1997 | Haber et al. | |
| 5,709,432 A | 1/1998 | Gryp | 297/411.32 |
| 5,720,966 A | 2/1998 | Ostendorf | |
| D392,466 S | 3/1998 | Kendall et al. | |
| 5,727,278 A | 3/1998 | Per-Lee | |
| 5,727,728 A | 3/1998 | Sainz et al. | |
| 5,744,149 A | 4/1998 | Girardot | |
| 5,784,747 A | 7/1998 | Girardot et al. | |
| 5,795,644 A | 8/1998 | Delarosa | |
| 5,802,655 A | 9/1998 | Denton | |
| 5,804,539 A | 9/1998 | Gordon et al. | |
| 5,839,842 A | 11/1998 | Wanat et al. | |
| 5,857,794 A | 1/1999 | Chien | |
| 5,895,163 A | 4/1999 | Chapman | |
| 5,897,543 A | 4/1999 | Francis | |
| 5,916,661 A * | 6/1999 | Benson et al. | 428/131 |
| 5,980,931 A | 11/1999 | Fowler et al. | |
| 6,012,411 A * | 1/2000 | Hochbrueckner | 116/207 |
| 6,015,242 A | 1/2000 | Gillis | |
| 6,042,288 A | 3/2000 | Rattinger et al. | |
| 6,045,882 A | 4/2000 | Sandford | |
| 6,048,407 A | 4/2000 | Schoch | |
| 6,087,279 A * | 7/2000 | Laun | 15/209.1 |
| 6,132,841 A | 10/2000 | Guthrie et al. | |
| 6,209,165 B1 | 4/2001 | Frolova | |
| 6,210,062 B1 | 4/2001 | Kokubo | |
| 6,227,742 B1 | 5/2001 | Corn et al. | |
| 6,267,524 B1 | 7/2001 | Kroha | |
| 6,318,922 B1 | 11/2001 | Briggs | |
| 6,321,750 B1 * | 11/2001 | Kelly | 128/844 |

FOREIGN PATENT DOCUMENTS

| | | |
|---|---|---|
| EP | 0 653 635 A1 | 5/1995 |
| EP | 0 728 475 A2 | 8/1996 |
| EP | 0 873 711 A2 | 10/1998 |
| EP | 0 340 993 | 11/1999 |
| EP | 1 040 803 | 10/2000 |
| EP | 1 125 541 A | 8/2001 |
| EP | 1 301 284 B1 | 4/2003 |
| FR | 1364891 | 10/1964 |
| JP | 06160486 | 1/1966 |
| NZ | 206330 | 5/1986 |
| NZ | 206331 | 5/1986 |
| WO | WO 89/07935 | 9/1989 |
| WO | WO 94/12088 A1 | 6/1994 |
| WO | WO 95/00116 | 1/1995 |
| WO | WO 95/26670 | 10/1995 |
| WO | WO 96/04836 | 2/1996 |
| WO | WO 96/10429 | 4/1996 |
| WO | WO 96/11673 | 4/1996 |
| WO | WO 96/23439 | 8/1996 |
| WO | WO 97/07780 | 3/1997 |
| WO | WO 97/07781 | 5/1997 |
| WO | WO97/24053 | 7/1997 |
| WO | WO 97/35564 | 10/1997 |
| WO | WO 97/38843 | 10/1997 |
| WO | WO 98/14442 | 5/1998 |
| WO | WO 98/18441 | 5/1998 |
| WO | WO 98/18444 | 5/1998 |
| WO | WO 98/18445 | 5/1998 |
| WO | WO 98/18446 | 5/1998 |
| WO | WO 98/28399 | 7/1998 |
| WO | WO 98/50012 | 11/1998 |

| WO | WO 98/55109 | 12/1998 |
| --- | --- | --- |
| WO | WO 99/09873 | 3/1999 |
| WO | WO 00/75035 | 12/2000 |
| WO | WO 01/85002 A1 | 11/2001 |
| WO | WO 02/07900 A1 | 1/2002 |

OTHER PUBLICATIONS

European Search Report, dated Sep. 16, 2002 for EPO Appln. No. EP 02254106.

U.S. patent application Ser. No. 09/879,931,(JBP–550), Johnson & Johnson Consumer Companies, Inc.

Rosato, D.V., Rosato's Plastics Encyclopedia and Dictionary, *Hanser Publishers, NY*, 1993, p. 119.

Label–Neutrogena Rainbath Body Polishing Sponge–published before Feb. 14, 2000.

Decision from ROC Intellectual Property Office Dated Mar. 8, 2004 for Taiwan Appl. No. 90103188.

Gollnick H., Topical Drug Treatment in Acne, Dermatology, 196, 119–125 (1998).

\* cited by examiner

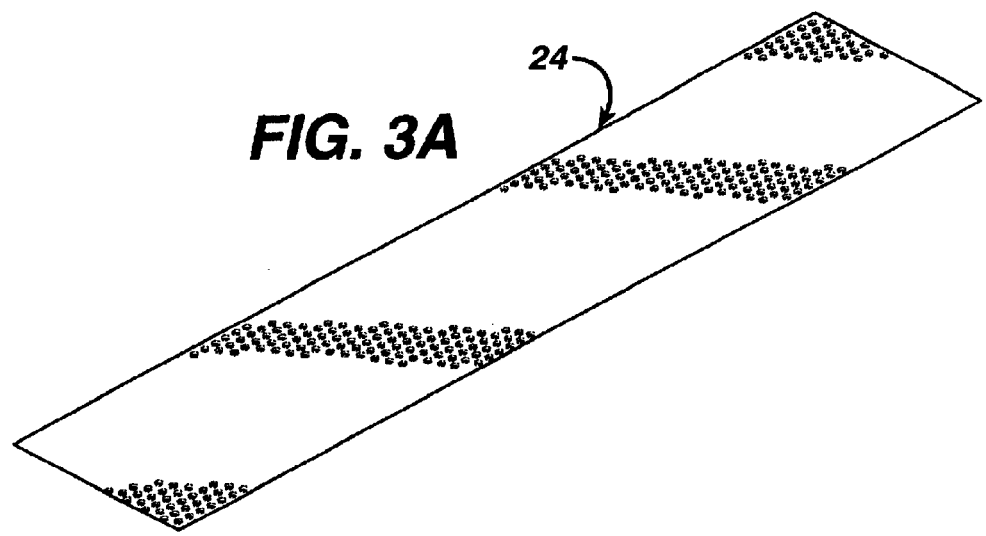
FIG. 3A
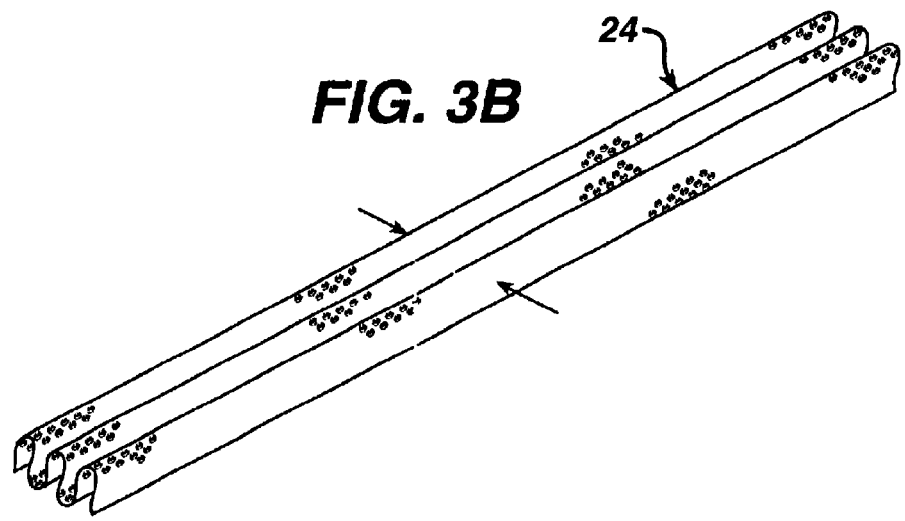
FIG. 3B
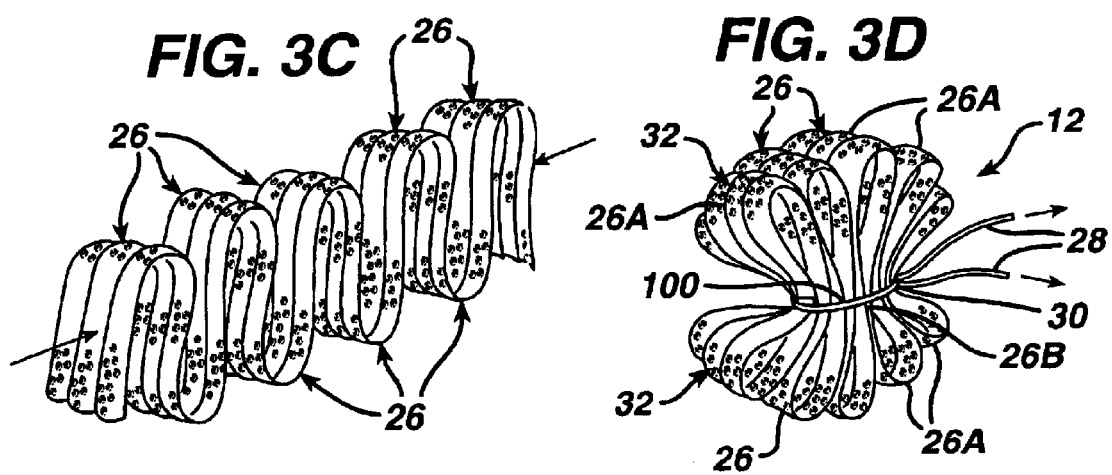
FIG. 3C
FIG. 3D

TEXTURED FILM DEVICES

BACKGROUND OF THE INVENTION

1. Field of the Invention

This invention is generally related to the field of cleansing and scrubbing devices, and methods for their use and manufacture. More particularly, this invention is related to soft, textured film devices for personal hygiene, and methods for their use.

2. Description of the Prior Art

Recently liquid personal washing cleansers have become popular. However, it is difficult to use such liquid cleansers without a tangible washing implement.

One known cleansing implement includes the sponge, see e.g., U.S. Pat. No. 4,627,129 (reticulated polyurethane foam sponge). However, such sponges tend to retain moisture and cleansing materials and thus promote mold and microbial growth.

Another known cleansing implement includes the polymer mesh puffs, see e.g., U.S. Pat. Nos. 5,727,278, 5,709,432, 5,144,744, and 5,784,747. However, such puffs tend to be rather abrasive and rough on the skin.

Yet another known cleansing implement is a "closed sandwich" structure comprised of two substrate layers bonded together to form a plurality of compartments for soap and the like as disclosed in U.S. Pat. No. 4,515,703. However, because these devices have a relatively low open area, they are capable of producing only a relatively small amount of foam and also tend to retain moisture.

It would be desirable to have a device that would not only be gentle to the skin but would also not retain moisture and would produce superior lather when used with a typical liquid cleanser.

SUMMARY OF THE INVENTION

In accordance with this invention, there is provided a device comprising:

a. at least one gathered piece of textured film having textured variations; and b. a securing means for substantially permanently holding the at least one gathered piece of textured film together.

Another embodiment of the present invention is directed to a device comprising:

at least one piece of textured film, wherein the device is in the form of a spherical poof, a mitt a cloth having at least 1.3 textured variations/cm$^2$, a glove, a plurality of textured film appendages attached to a holding means or a textured film pad attached to a holding means.

The devices of this invention are not only gentle to the skin but also capable of creating superior lather when used with a typical liquid cleanser.

DESCRIPTION OF THE DRAWINGS

The invention will be more fully understood and further advantages will become apparent when reference is made to the following detailed description of the invention and the accompanying drawing in which:

FIG. 3A is a representation of an unfolded sheet of textured film.

FIG. 3B. is a representation of the sheet of FIG. 3A being pleated in a transverse direction.

FIG. 3C. is a representation of the sheet of FIG. 3B being folded onto itself in a longitudinal direction in order to form ruffles.

FIG. 3D. is a representation of the sheet of FIG. 3C being drawn inwardly toward the center of the ruffles by a string.

DETAILED DESCRIPTION OF PREFERRED EMBODIMENTS

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

As used herein, the term, "texture variations," shall mean holes or embossments in the film. The term, "nonwoven web," shall mean a web of material that is formed without the aid of a knitting or a textile weaving process, and the term, "fabric" shall refer to all of the woven, knitted, and nonwoven fibrous webs. As used herein, the term, "width," shall mean the diameter when referring to generally circular apertures/holes or the largest distance across a given shape when referring to non-circular apertures/holes.

Figure 1:
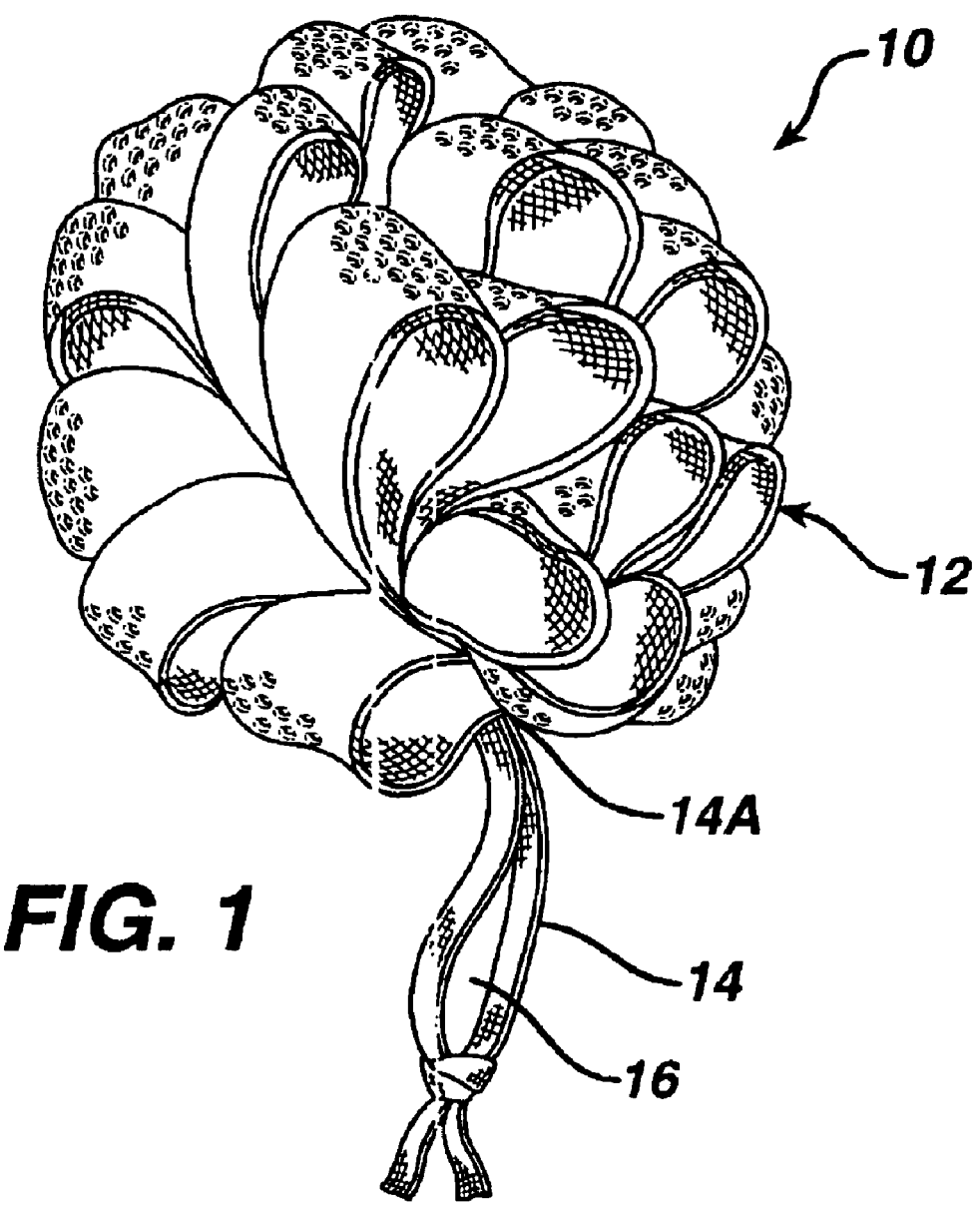
FIG. 1 is a representation of the cleansing device of the present invention with closed-ended ruffles, which may be formed in accordance with the method illustrated in FIGS. 2A-2C.

Referring to the drawings and particularly to FIG. 1, there is illustrated a cleansing or scrubbing device, generally designated 10, of the present invention. In general, the cleansing device 10 includes a body 12 of gathered, flexible textured film, an optional holding means 14 for the user, and a securing means 28 (not shown) for substantially permanently holding the film together in the desired gathered arrangement. As used herein, "substantially permanently" means a period of time at least as long as the film of the device is suitable for cleansing uses. By "gathered," it is meant to fold, pleat, smock, or any other known technique for pulling the film together into the desired shape. By "textured film" it is meant any film with embossments, perforations or apertures and the like, with apertures being preferred.

Examples of suitable textured films include but are not limited to those comprised of polyethylene, polypropylene, ethylene vinyl acetate copolymer, metallocene polyethylene, and blends and copolymers thereof. Examples of suitable commercial perforated films include those available from Tredegar Film Products, Inc. under the tradename, "VisPore®," from Polymer Group, Inc. under the tradename, "Reticulone®, or from Guial Inc. under the tradename,"Veole" with the "VisPore®" film being preferred.

Figure 7:
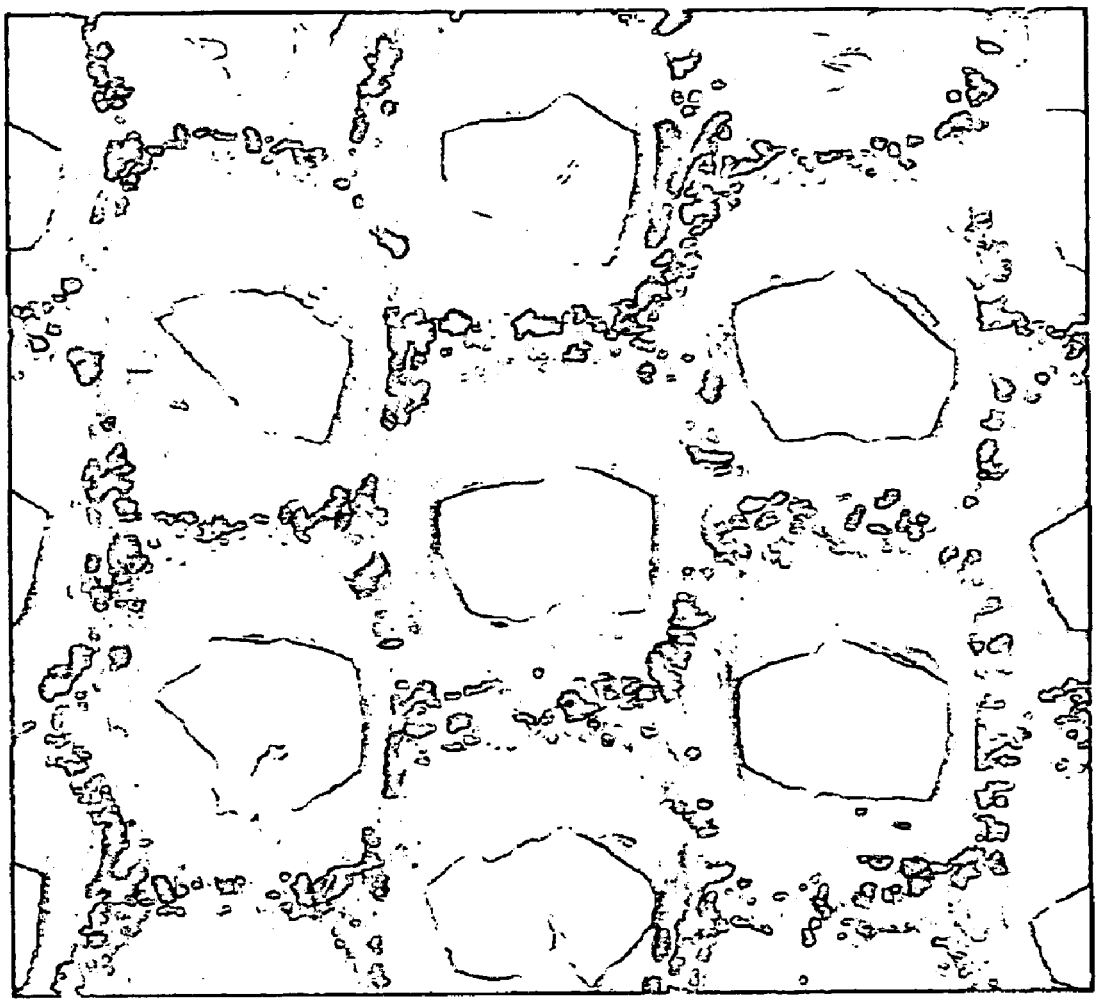
FIG. 7 is a micrograph of the apertured film suitable for use in the puff of the present invention as viewed from the front, "smooth" side, wherein the original photomagnification is 12.5×.
Figure 8:
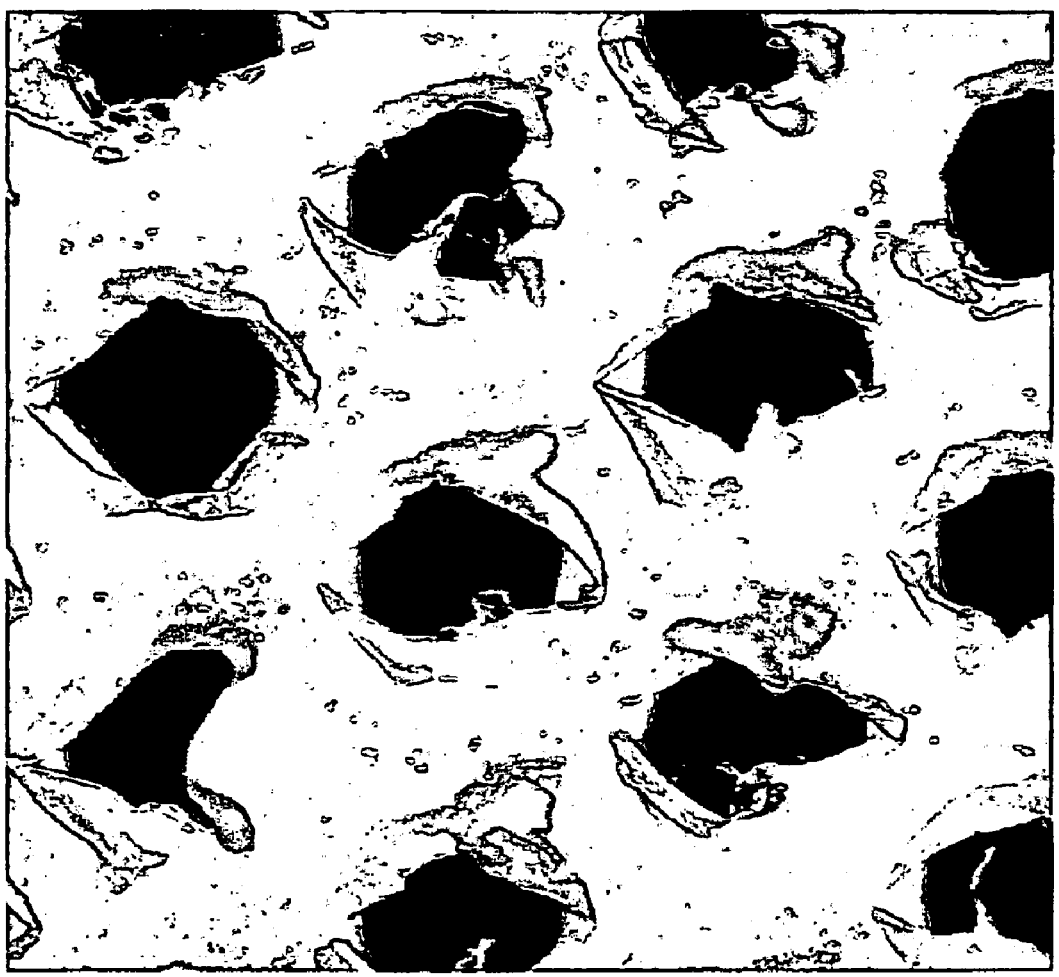
FIG. 8 is a micrograph of the apertured film suitable for use in the puff of the present invention as viewed from the back, "rough" side, wherein the original photomagnification is 12.5×.

The pores and embossments of the textured films may be created in the films via known processes, see, e.g., U.S. Pat. Nos. 3,054,148; 4,741,877; 3,929,135 and 3,394,211 or via a post treatment perforation step, see U.S. Pat. Nos. 3,929, 135 and 3,394,211 (blast of heated air creates a pressure differential across a perforated forming surface covered with a pre-formed film). Generally speaking, the resulting textured film possesses a "rough" side, which contains the raised protuberances as shown in the micrograph of the apertured film in FIG. 8, and an opposing "smooth" side as shown in the micrograph of the apertured film in FIG. 7. By "smooth" side, it is meant the side from which the raised protuberances originate. The protuberances in such apertured films are generally cone-shaped. In uses of the devices of the present invention where exfoliation is of importance, it is preferable to have the protuberances facing outward.

Figure 5:
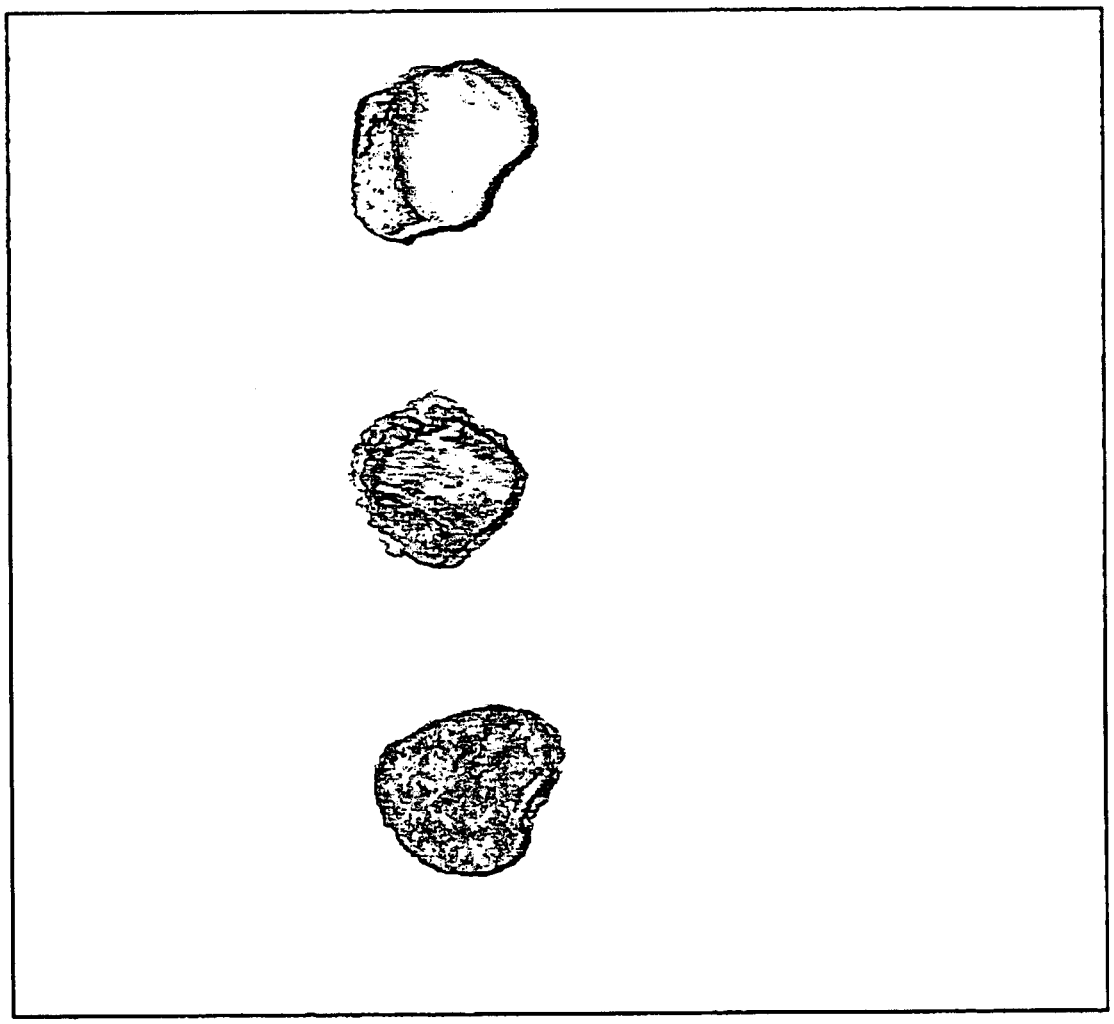
FIG. 5 is a micrograph of the cross-section of single filaments of the puff of FIG. 4, wherein the original photomagnification is 80×.
Figure 6:
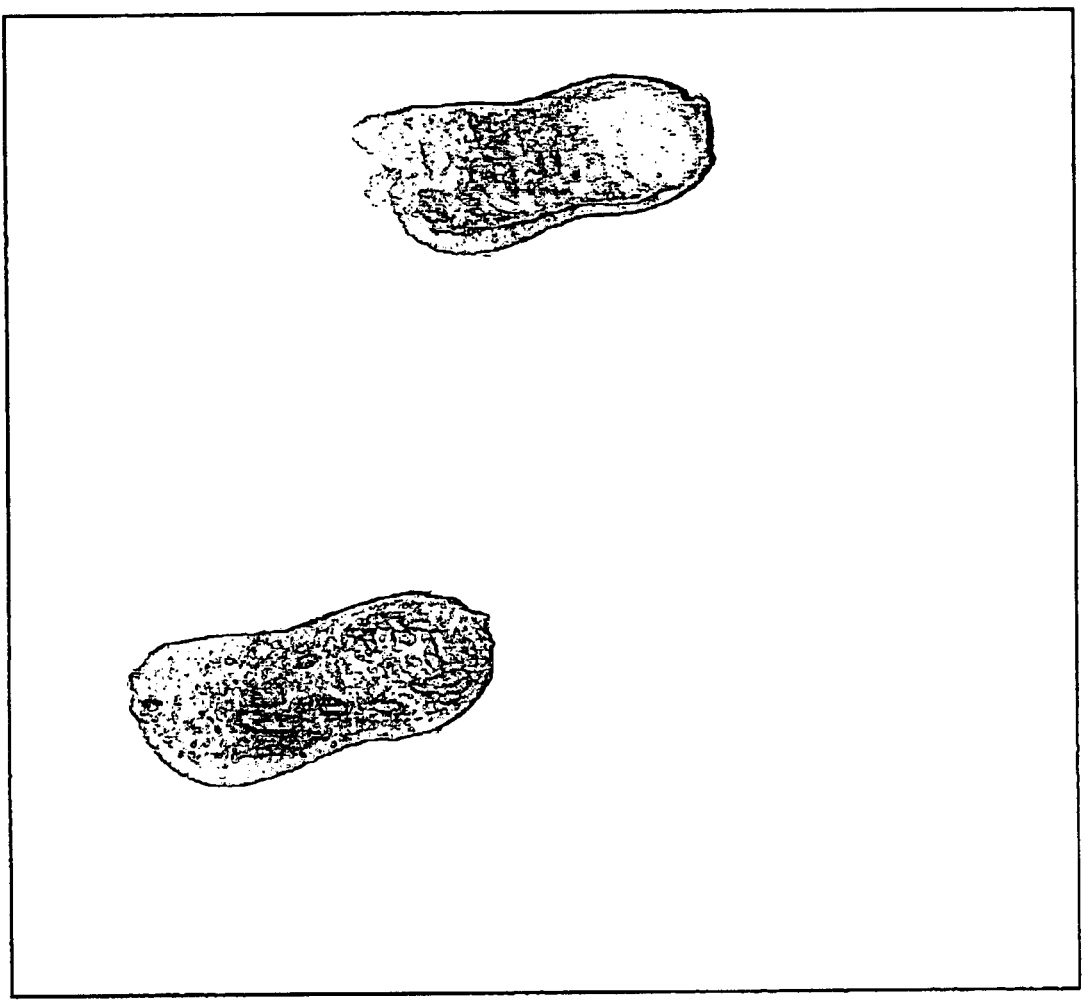
FIG. 6 is a micrograph of the cross-section of the puff of FIG. 4 located at B, which is where the individual filaments are joined to form the mesh, wherein the original photomagnification is 80×.
Figure 9:
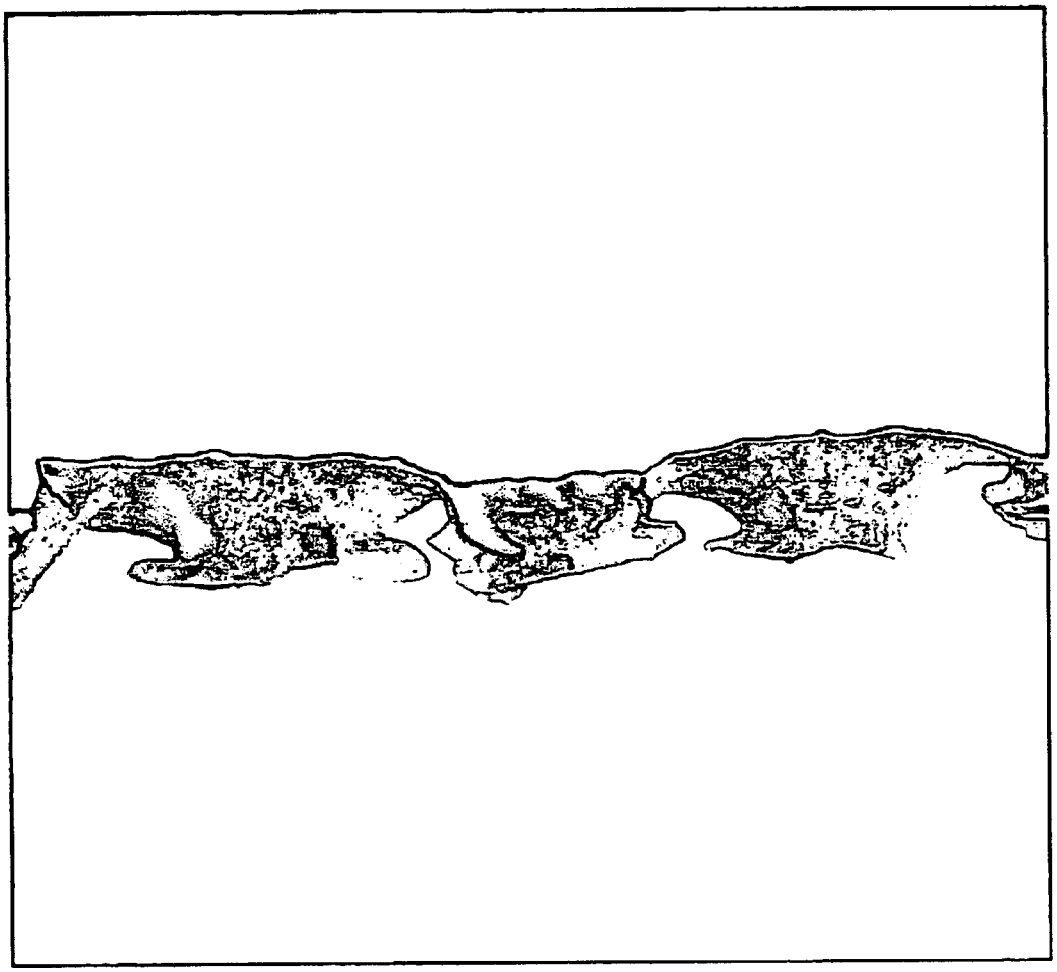
FIG. 9 is a micrograph of the cross-section of the film of FIG. 7, wherein the original photomagnification is 12.5×.

As shown in FIG. 9, the cross-sectional view of the apertured films suitable for use in the devices of the present invention illustrates that the textured films are three-dimensional. By contrast, both FIG. 5 and FIG. 6 illustrate that the mesh used in the prior art has essentially a two-dimensional cross sectional shape. FIG. 5 illustrates that the diamond mesh netting used in prior art polymeric puffs is comprised of individual filaments having a round or kidney-shaped cross-sectional shape. Moreover, as shown in FIG. 6, the areas of the diamond mesh netting where the filament strands are joined have a dumbbell-like cross-sectional shape. As a result of using a three-dimensional textured film in the devices of the present invention, the devices are significantly lighter than those prior art meshed poufs of similar overall size and shape.

Although the type of texture variations, as well as their depth and width, in the textured film may vary depending upon, for example, the type of active material to be used with the device, the desired rate at which active material, e.g., soap, to be released to the surface of the device, the ease of rinsability desired, the desired end use of the device, the size of bubbles desired, and the volume of foam desired, generally the textured film contains from about 1.6 textured variations/$cm^2$ to about 248 textured variations/$cm^2$, preferably from about 3 textured variations/$cm^2$ to about 30 textured variations/$cm^2$, and most preferably from about 5 textured variations/$cm^2$ to about 15 textured variations/$cm^2$. Preferably, for uses of the devices on locations such as the face, where softness is of concern, the film contains from about 80 texture variations/$cm^2$ to about 200 texture variations/$cm^2$. Preferably, for uses of the devices on locations such as the arms, where volume of foam is of concern, the film contains from about 5 texture variations/$cm^2$ to about 15 texture variations/$cm^2$. In alternative embodiments of the device of the present invention, e.g., a cloth, glove, or mitt, it is preferable to have textured variations of from about 1.3, preferably about 1.4, and more preferably about 4.5 texture variations/$cm^2$ to about 15 texture variations/$cm^2$.

The size of the texture variations, measured as the average width of the texture variations across the smooth side of the textured film, ranges in size from about 0.04 cm to about 0.6 cm, and preferably from about 0.1 cm to about 0.4 cm, and more preferably from about 0.2 cm to about 0.35 cm. In embodiments where it is desirable to slowly deplete the soap from the device, it is preferable to use texture variations having a relatively smaller average width, i.e. less than about 0.1 cm.

"rough" side of the apertured film divided by the total area examined. Typically, the open area property of a film is expressed in terms of "% open area," which is equal to 100×area fraction.

One type of textured film suitable for use in the devices of the present invention further possesses general mechanical properties as shown below in Table A:

TABLE A

Mechanical Properties - Perforated Films

| Type of Material | Force to stretch to 20% elongation* N/m (lb./in) | Force to stretch to 50% elongation* N/m (lb./in) | Direction of Stretch | Tensile Strength* N/cm (lb./in) | Elasticity# |
|---|---|---|---|---|---|
| Perforated Film suitable for use in present invention | 35–263 (0.2 to 1.5) and preferably 35–175 (0.2 to 1.0) | 88–350 (0.5 to 2.0) and preferably 88–263 (0.2 to 1.5) | Machine | >263 (>1.5) | About 60% - less than about 100%, and preferably from about 80% to less than about 100% |

*Using ASTM D-882
Measured by the % recovery from a 50% elongation using an instron testing machine The depth of the embossment texture variations, as measured from the "smooth" side of the apertured film to the bottom of the embossment, may range from about greater than about 0 cm to about 0.4 cm, and preferably between about 0.005 cm to about 0.3 cm. In embodiments wherein rinseability is of concern, it is preferable to use either an apertured film or an embossed film having a depth of embossment of greater than about 0.05 cm.

The textured variations may be of any shape that can perforated or embossed into the film. Although the shape of the textured variation will generally depend upon, for example, aesthetics, the type of active material to be used with the device, the desired rate at which the active material, e.g., soap, to be released to the surface of the device, the ease of rinsability desired, the desired end use of the device, the size of bubbles desired, and the volume of foam desired, the shape of the textured variation, as it appears on the "smooth" side of the film, is typically in the general form of circles, honeycombs, hearts, pears, squares, hexagons, triangles, pentagons, stellates, rectangles or combinations thereof, with the general circular shapes and hexagonal shapes being most preferred.

Although the post-textured basis weight of the film may vary depending upon, for example, the desired end use of the device and the desired aesthetic appearance and feel of the device, generally the textured film has a basis weight of about 10 g/m$^2$ to about 80 g/m$^2$, and preferably from about 20 g/m$^2$ to about 50 g/m$^2$.

Apertured films suitable for use in the devices of the present invention have an open area of no more than about 45%, and preferably greater than about 15% and no more than about 35%, based upon the total area (both film and void space) of the apertured film. As used herein, "open area" is a measure of the void space or area fraction. "Area fraction," as used herein, may be calculated as the sum of the areas of the exit openings of the protuberances on the We have unexpectedly found that the three dimensional devices made from textured films having the above characteristics were not only very soft and gentle to the skin, but were capable of producing a large quantity of pleasing lather. Moreover, when the resulting devices were rubbed against a desired surface or squeezed during use with soap and other cleansing products, the soap and other cleansing products propagated well throughout the structure of the devices 10.

Without wishing to be bound by theory, we believe that the structure of the textured film used in the device of the present invention contributes to its superior soft feel relative to that possessed by prior art diamond mesh filament netting devices. More specifically, the devices of the present invention are comprised of perforated films that are relatively flat and smooth, whereas the known mesh netting devices are comprised of a rough fibrous netting material.

In general, the spherical device 10 of the present invention may be made by gathering the textured film in any desired manner so as to produce a desired gathered arrangement of textured film, followed by securing the resulting gathered arrangement. As shown in FIG. 3C, one method for forming the spherical device 10 is via folding or pleating at least one sheet 24 of a suitable flexible textured film upon itself to provide a multiplicity of ruffles 26 bunched together so as to define the body 12. The body 12 is then secured preferably around the center, which in FIG. 3D is shown by string 28.

In a preferred embodiment, the body may be formed by "C-folding" the textured film prior to gathering. In this embodiment, it is possible to control whether or not the textured variations are outward-protruding, and thus forming a device especially suitable for exfoliation, or inward protruding, and thus forming a soft, smooth-surfaced device suitable, for example, for gentle cleansing.

Figure 2A:
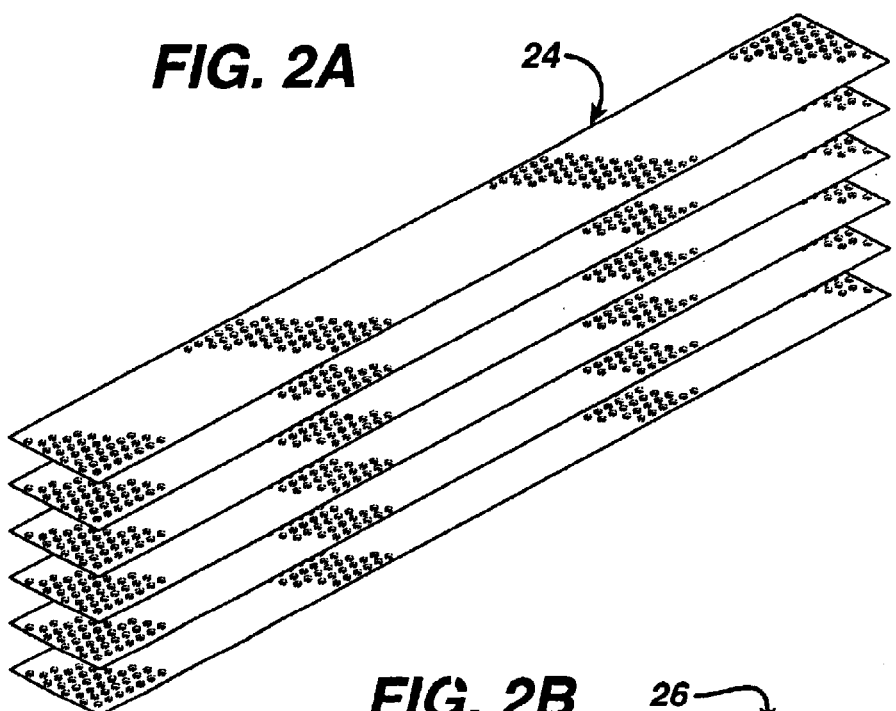
FIG. 2A is a representation of a plurality of textured film strips stacked one on top of each other.
Figure 2B:
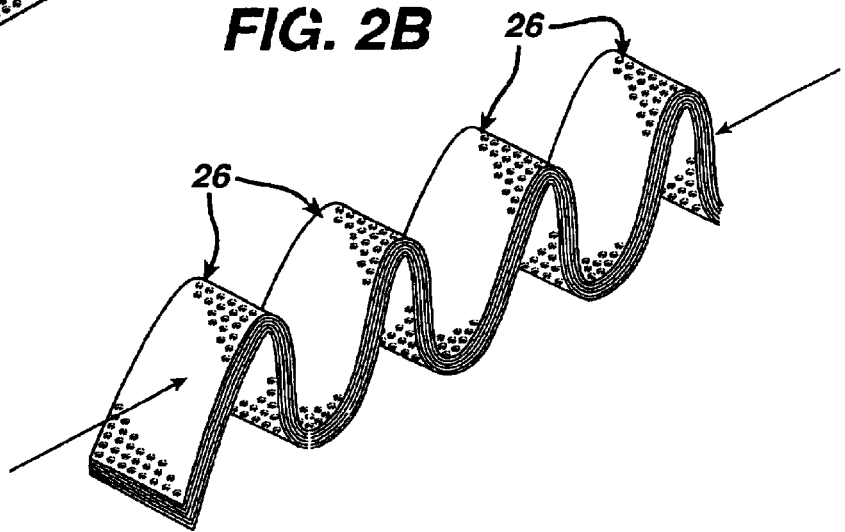
FIG. 2B. is a representation of the layered strips of FIG. 2A being pleated in a direction perpendicular to its longitudinal axis in order to form ruffles.
Figure 2C:
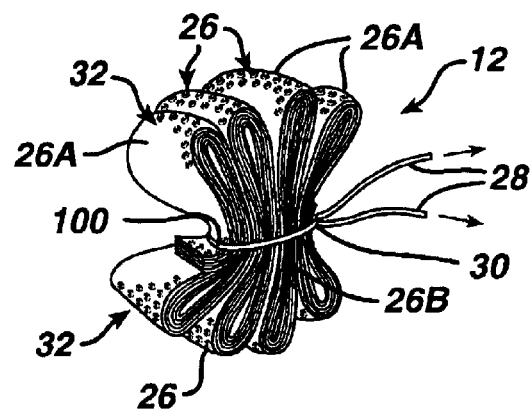
FIG. 2C. is a representation of the pleated layered strips of FIG. 2B being drawn inwardly toward the center of the ruffles by a string.
Figure 4:
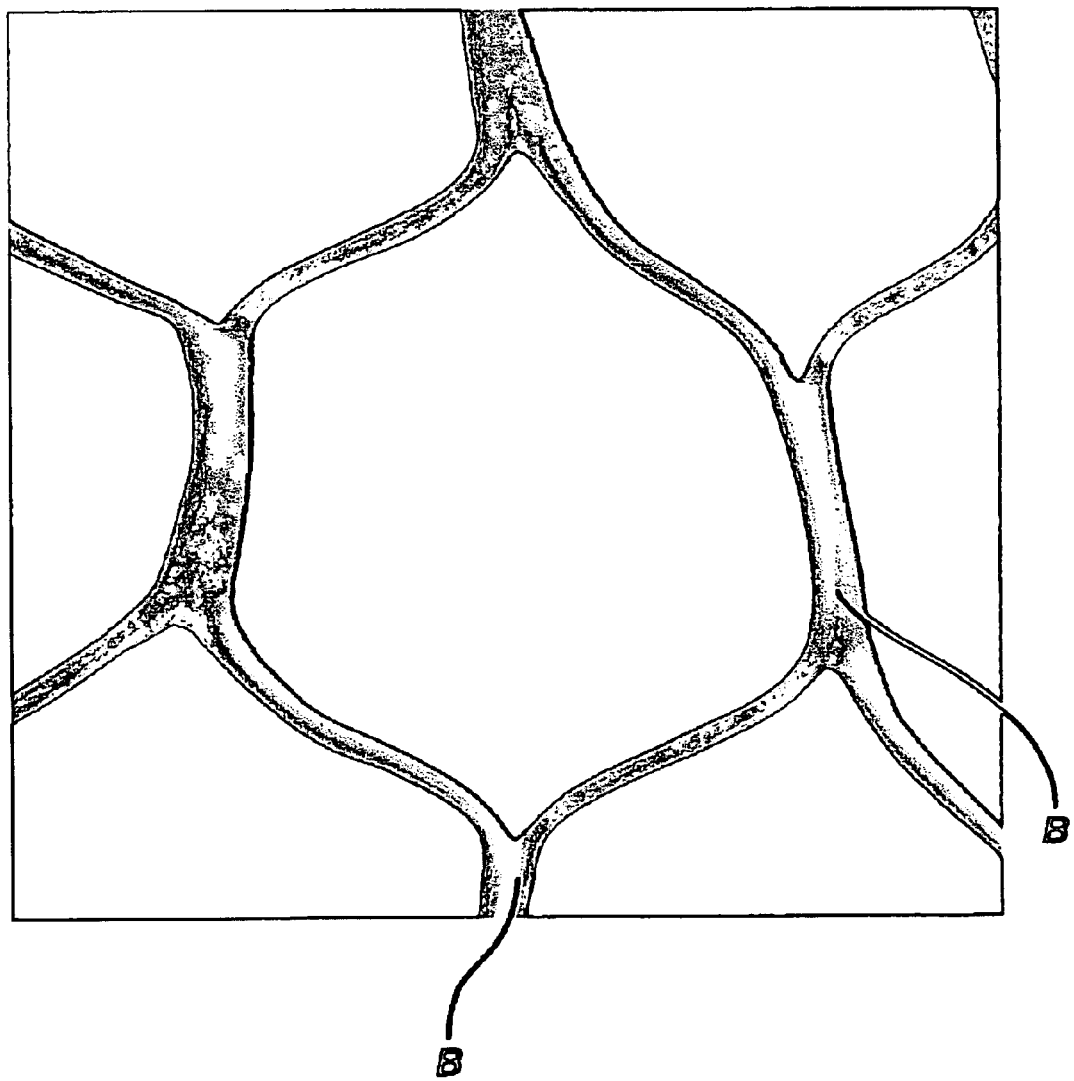
FIG. 4 is a micrograph of a diamond meshed film used in the prior art polymeric puffs, wherein the original photomagnification is 12.5×.

In an alternative embodiment, the body 12 of the device 10 may be formed by a plurality of stacked textured film sheets 24 folded upon themselves in order to form a multiplicity of ruffles 26 as shown in FIGS. 2A to 2C. Loop ends 26A of the ruffles 26, which are generally disposed at the exterior of the body 12, are capable of contacting preferably the skin of a user's body, or any desired object or surface, e.g. surfaces found in the home, boat, or automobile. Interior portions 26B extend between the loop ends 26A.

Figure 13A:
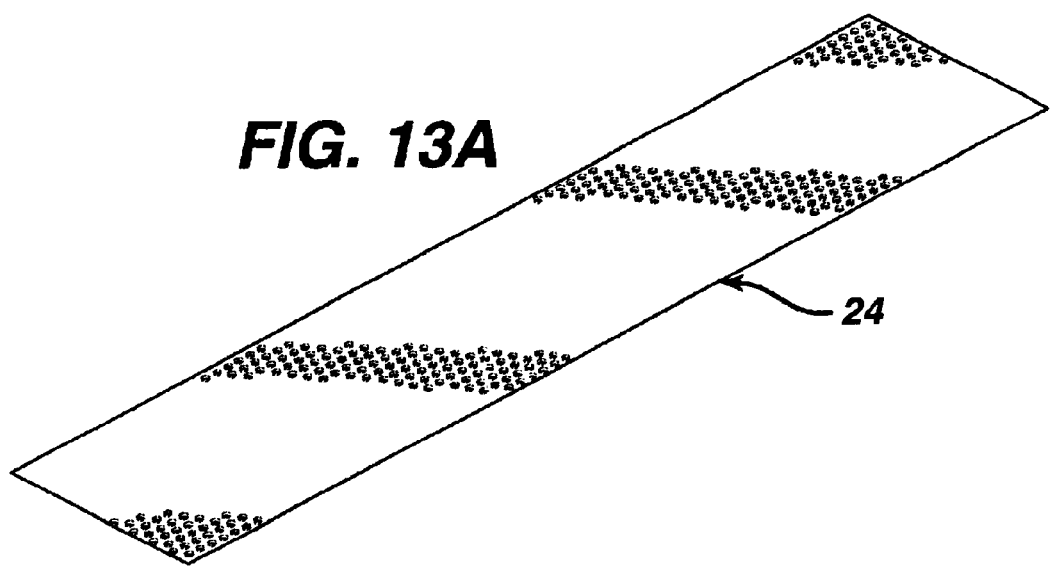
FIG. 13A is a representation of an unfolded sheet of textured film.
Figure 13B:
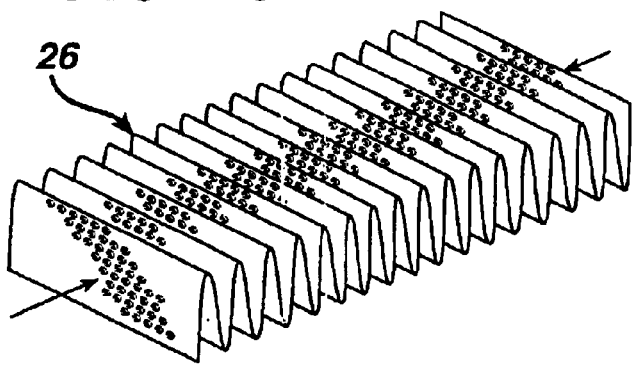
FIG. 13B. is a representation of the sheet of FIG. 13A being pleated in a direction perpendicular to its longitudinal axis.
Figure 13C:
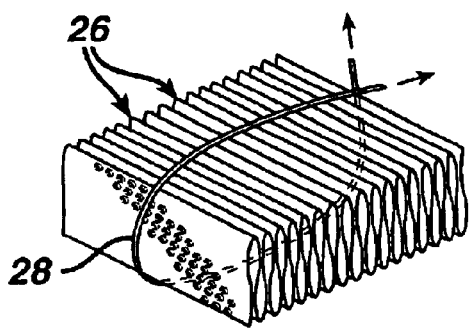
FIG. 13C. is a representation of the sheet of FIG. 13B having a string wrapped around the pleats as formed in FIG. 13B in order to form ruffles.
Figure 13D:
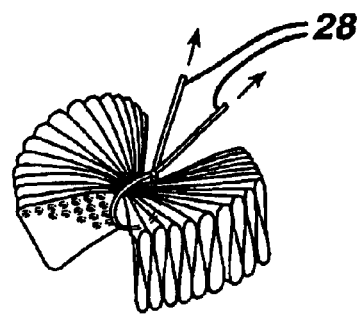
FIG. 13D is a representation of the sheet of FIG. 13C being drawn inwardly toward the center of the ruffles by a string.
Figure 14:
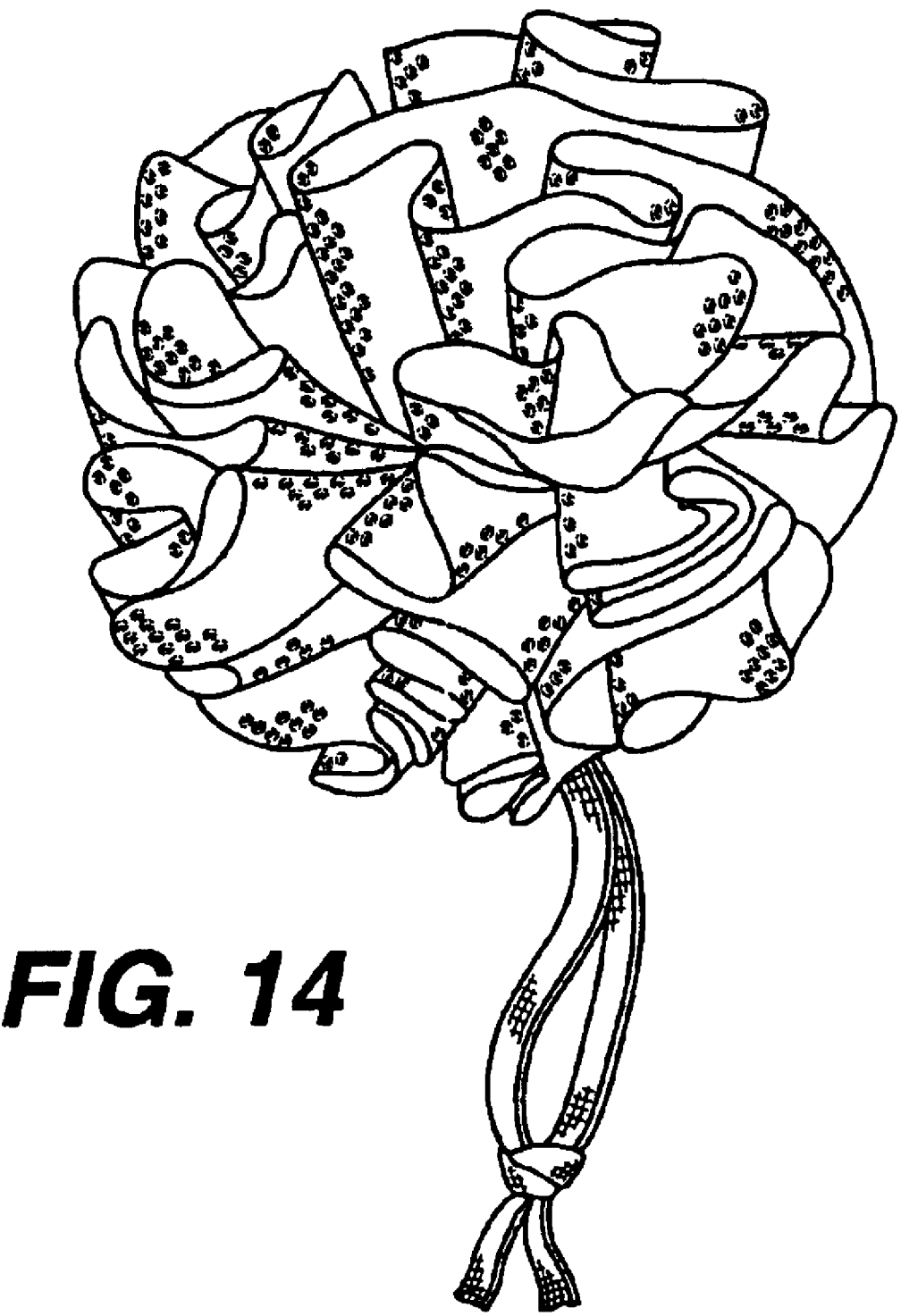
FIG. 14 is a representation of the puff having open-ended ruffles, which may be formed in accordance with the method illustrated in FIG. 13.

FIG. 2A shows the stack of textured strips in an unfolded condition, with the sheets disposed adjacent to one another, with one above the other. In an alternative embodiment (not shown), the textured film strips may be connected as in an accordion-type fold configuration. FIG. 2B shows the plurality of stacked sheets folded onto themselves in a direction which extends generally transverse to the longitudinal direction of the strips and which results in the formation of the multiplicity of ruffles 26 in a bunched together, folded condition. As shown in FIG. 2C, the bunched stack of textured film strips may be drawn inwardly toward a center to form the multiplicity of ruffles 26 by the securing means 28. An alternative method for gathering the film is demonstrated in FIGS. 13A through 13D, wherein the film is first gathered in a longitudinal or lengthwise direction, then the gathers are secured to form ruffles as shown in FIG. 13D. The ruffles 26 of the secured device may be adjusted to form the device into the desired shape.

Figure 15:
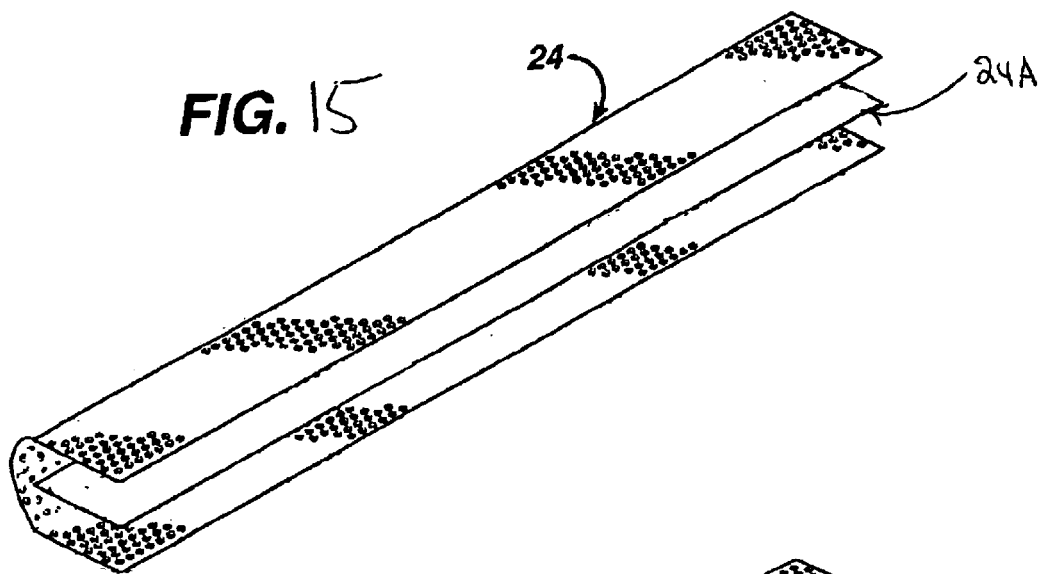
FIG. 15 is a representation of a cleansing device of the invention wherein the inner sheet is substantially covered via wrapping the outer sheet around the inner sheet, e.g., in a C-fold arrangement.
Figure 16:
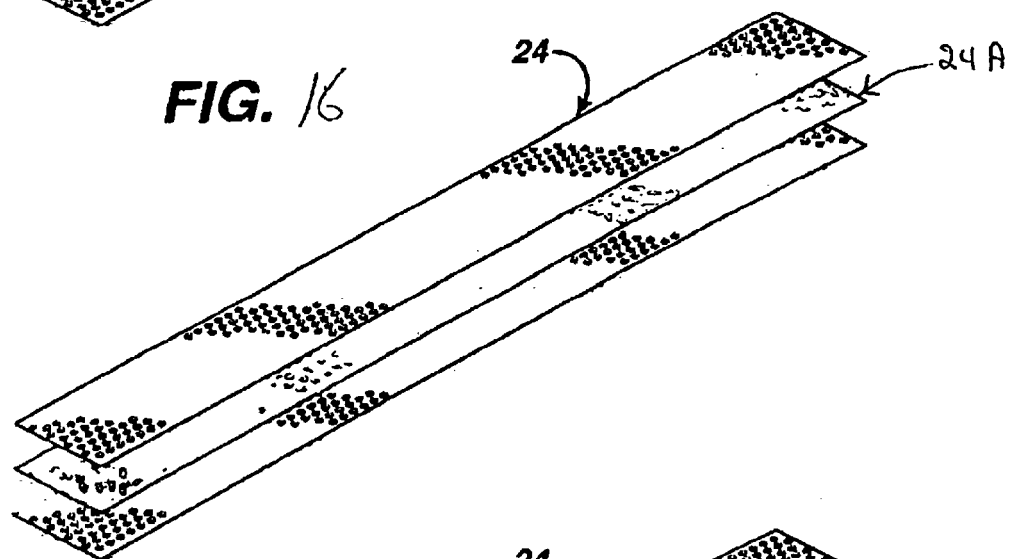
FIG. 16 is a representation of a cleansing device of the invention wherein the body of the device is formed by a plurality of stacked textured film sheets.

In an alternative embodiment, the body 12 of the device 10 may be formed by a plurality of stacked textured film sheets 24 and 24A as shown in FIG. 16, and more preferably by at least a pair of inner and outer sheets folded upon themselves to a multiplicity of ruffles 26 (not shown). Although at least one of the sheets must be comprised of the textured film, it is preferable to have the inner sheet being comprised of a material capable of giving the body rigidity disposed at the interior of the body 12 and the outer sheet being preferably comprised of a suitable textured film exposed at the exterior of the body 12 and substantially covering the inner sheet 24A. By "substantially covering," it is meant that enough of the inner sheet 24A is covered with the outer sheet so as to produce the desired end effects, e.g. sufficient foam, exfoliation, and/or softness. One method for "substantially covering" the inner sheet 24A is via wrapping the outer sheet 24 around the inner sheet, e.g., in a C-fold arrangement as shown in FIG. 15.

As described in U.S. Pat. No. 5,727,278, a multi-layered device may be made by arranging a pair of outer and inner sheets in an unfolded condition, with the sheets disposed adjacent to one another, with one above the other. The pair of outer and inner sheets may be then gathered, i.e. via folding and pleating, onto itself in a first direction. The pair of outer and inner sheets may then be folded yet again onto itself in a second direction, which extends generally transverse to the first direction and which results in the formation of a multiplicity of ruffles 26 in a bunched together, folded condition. Then, the pair of outer and inner sheets may be drawn inwardly toward the center of the multiplicity of ruffles 26 by a securing means 28.

Sheet-like materials that are capable of giving the body rigidity include a substantially coarse mesh, such as that used in known diamond mesh puffs, porous foams, reticulated foams, natural fibers (e.g. wood, or cotton fibers), synthetic or polymeric fibers (e.g. polyester or polypropylene fibers) which may or may not be textured, combinations thereof and the like. The fibrous sheets may be comprised of either woven or nonwoven fabrics. For example, the sheet may be comprised of a spunbonded or meltblown web or polyolefin fibers or may be a bonded-carded web comprised of natural and/or synthetic fibers. The polymeric sheets may be comprised of any of the polymers set forth above for use in the textured film. Preferably, these materials are used as the inner sheet disposed adjacent to and underneath the outer textured film sheet, or more preferably are inserted between two layers of textured film sheets so as to preserve the soft nature of the device.

Figure 17:
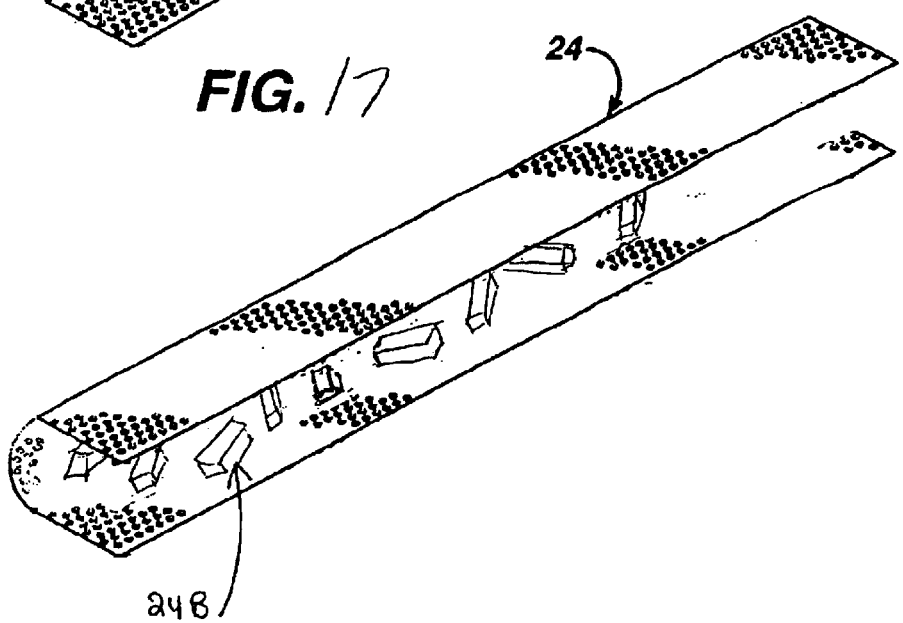
FIG. 17 is a representation of a cleansing device of the invention wherein the inner substrate is of a non-sheet form, such as a three-dimensional body comprised of solids, semi-solids, foams, shredded film or fibers, and combinations thereof.

In an alternative embodiment, the inner substrate may be of a non-sheet form, such as a three-dimensional body 24B comprised of solids, semi-solids, foams, shredded film or fibers, and combinations thereof as shown in FIG. 17. Any polymer that may be formed into a three-dimensional form would be especially suitable for use in this invention, such as those set forth above for use in the textured film. The inner substrate is preferably substantially covered by the outer textured sheet. By "substantially covered," it is meant that enough of the inner substrate is covered with the textured sheet so as to produce the desired end effects, e.g. sufficient foam, exfoliation, and/or softness. The outer textured film may be secured to the inner substrate via any of the securing methods set forth below.

The device 10 may be secured by any securing methods known in the art capable of securing the gathered textured film, e.g., the ruffles 26 in 3D, in a desired arrangement. Examples of suitable securing methods include heat sealing with a sealer capable of reaching a temperature greater than the melting temperature of the film; ultrasonic sealing; pressure sealing; tying with a ribbon, cord, strip, string such as see U.S. Pat. No. 5,727,278, band, and the like; applying hooks and loops such as that registered as "VELCRO", adhesive, elastic, tape such as double-sided adhesive tape, heat shrinkable film, or other known fastening device thereto; applying a locking tether thereto, see U.S. Pat. No. 5,784,747, and the like. Preferably the securing means is comprised of a tying or otherwise wrapping a cord, which is either elastic or inelastic, around the gathered arrangement as well as applying an adhesive-coated cord to the stretched state of the textured film. In the latter embodiment, the textured film becomes bunched together after it is released from its stretched state.

In embodiments wherein the securing means is a string, ribbon, or cord, such as that shown in FIG. 3D, the string 28 may be made from any suitable material, such as a separate strip of mesh netting, perforated film itself, nylon, or cotton. The string may be wound about a circumferential portion of the body 12, preferably centrally located, then drawn inwardly toward the center 100 of the body and secured to itself to form a winding of the string 28 with substantially smaller circumference than that of the body 12.

By winding the string 28, or applying any other suitable securing means, about the body 12, the interior portions 26B of the ruffles 26 become bunched together toward the center 100 of the body 12. As a result of this bunching effect, a central portion 30 is formed. A pair of lobes 32 formed of the loop ends 26A of the ruffles 26, which extend radially in every direction, project outwardly from the central portion

30. See U.S. Pat. No. 5,784,747. Because each loop end 26A generally has the same length, the lobes 32 of the body 12 formed thereby generally have a sphere-like shape. Due to the general pliability of the textured film material that makes up the body 12, the spherical shape of the body 12 is deformable during use of the cleansing device 10, e.g. the application of pressure and contacting of the device 10 to the desired surface to be cleaned in a scrubbing or scouring motion. Generally, the sphere-like shape of the body 12 will return after use without becoming separated.

Optionally, the device 10 may further comprise a holding means 14 to enable the user to hold the device during use. Examples of suitable holding devices nonexclusively include those disclosed in U.S. Pat. No. 5,727,278, as well as straps, handles, knobs, with looped straps being preferred. In an alternative embodiment, the holding means may be a character figure, such as a character's head, e.g., an animal or cartoon personality. In an alternative embodiment wherein the device is further comprised of a container for an active material, that container may also serve as the holding means.

In embodiments using a looped strap as the holding means, the strap is typically comprised of interwoven strands of flexible material and preferably has a substantially narrow and flat configuration. Preferably, the inner end 14A of the holding means is secured to the interior of the body 12 and thus is substantially hidden therewithin. The holding means 14 may be secured to the body 12 via any known securing methods such as those described above, with looping and tying being preferred. Preferably, the outer end of the strap 14 substantially extends beyond the exterior of the body 12. The strap 14 can be of any desired length but is preferably of a length suitable for forming a loop 16, which is large enough to permit a variety of hand sizes to fit therethrough. The material forming the strap can be either substantially inelastic or elastic.

In an embodiment using an elastic band as the securing means, it is preferable to leave an excess amount of band as unwrapped around the body 12 in order to form a looped strap 14 for the device 10.

Figure 10:
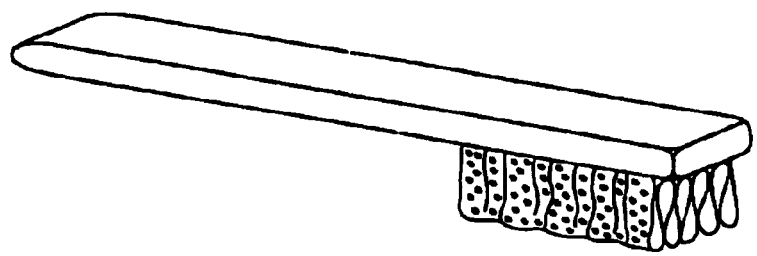
FIG. 10 is a perspective view of an alternative device of the present invention.
Figure 11:
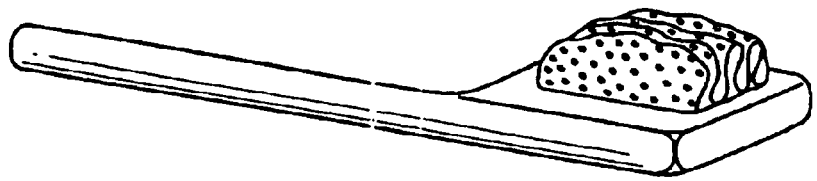
FIG. 11 is a perspective view of yet another alternative device of the present invention.
Figure 12:
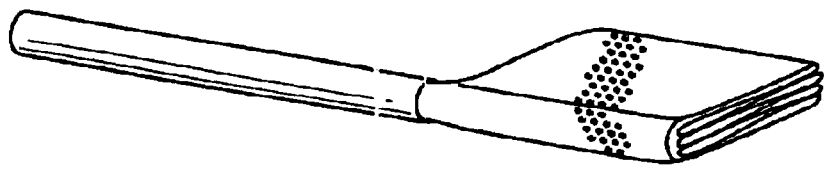
FIG. 12 is a perspective view of yet another alternative device of the present invention.
Figure 20:
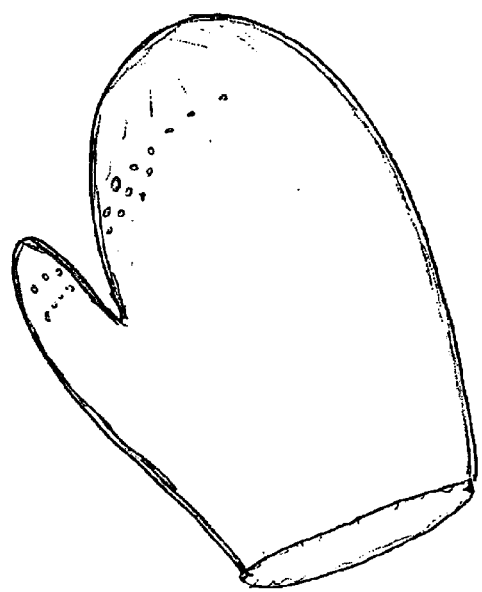
FIG. 20 is a representation of a cleansing device of the invention wherein the body of the device is in the form of a mitt.
Figure 18:
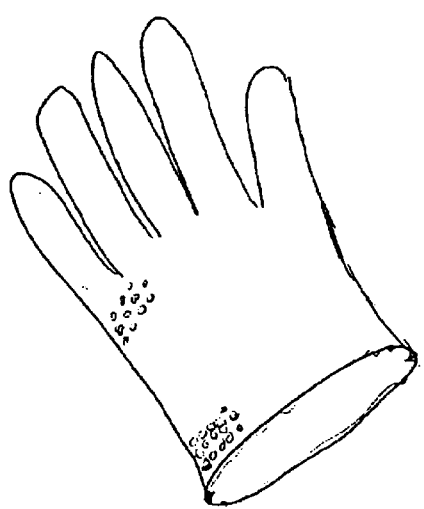
FIG. 18 is a representation of a cleansing device of the invention wherein the body of the device is in the form of a glove.
Figure 19:
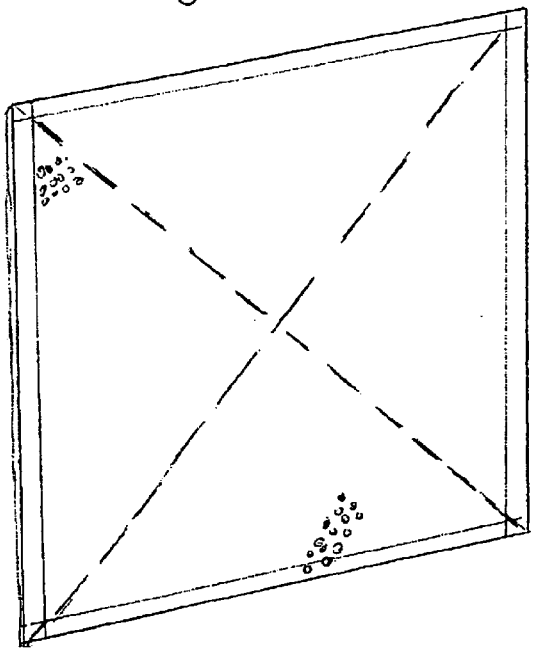
FIG. 19 is a representation of a cleansing device of the invention wherein the body of the device is in the form of a cloth.

In alternative embodiments of the present invention, the textured film may be formed into other devices such as a mitt such as that illustrated in FIG. 20; a glove such as that illustrated in FIG. 18; a cloth such as that illustrated in FIG. 19; strips/appendendages of textured film attached to a holding means, such as that illustrated in FIG. 10; and a device wherein the combination of at least one layer of textured film disposed on top of a secondary substrate is attached to a holding means such as that illustrated in FIG. 11. Examples of suitable secondary substrates include the textured films as well as any of the aforementioned substrates capable of giving the device 10 rigidity. Examples of holding means include all of those aforementioned. The textured film layer may be on top of the holding means, such as that illustrated in FIG. 11 or may extend from the holding means, for example, as a pad, such as that illustrated in FIG. 12, or any combination thereof (not shown). Any of the above-mentioned securing means may be used to secure the layer(s) of textured film, the secondary substrate, and the holding means together.

In the embodiments of the present invention wherein the device is a mitt or glove, such devices are comprised of a front face and a back face, wherein at least one of the faces is a textured film. The composition of the sheet for the front face may be the same or different as that for the sheet of the back face. In one embodiment wherein the mitts and gloves are comprised of a total of 2-plies of film sheets, the plies are either two separate substrates sealed together along the periphery as desired, or are one substrate that is first folded upon itself then appropriately sealed. Preferably, the gloves and mitts are comprised of a front face comprised of 2 or more plies of sheets and a back face comprised of 2 or more plies of sheets, with at least one of the outer plies being a textured film.

In an alternative preferred embodiment, each face of the gloves and mitts may be comprised of at least one ply of textured film, wherein the textured variation of one face is different from the textured variation of the other face. For example, in the latter embodiment, the one face may be comprised of a textured film with the protuberances facing outward and the other face may be comprised of same but with the protuberances facing inward toward the hand, in order to have an implement capable of either exfoliation or soft gentle cleansing. Alternatively, the outer ply of the textured film of one face may have smaller textured variations than the outer ply of the textured film of the other face.

In yet another alternative embodiment of the gloves or mitts having at least 2 plies/face, the textured variations of the two inner plies, i.e. those that touch the hand, may differ with respect to, for example, size of textured variations and/or orientation of textured variations, from those of the plies of the two outer faces, i.e. those that do not touch the hand. In this embodiment, reversability of the glove or mitt is a preferred attribute.

The plies of textured film in the mitts and gloves may be secured together via any of the forementioned securing techniques, with heat sealing of the edges being preferred. The mitts may be of any general shape with at least one opened end for a hand to enter, with the thumb portion being an appendage to the finger portion or alternatively being created by inwardly securing the plies to form a thumb-pocket. In an alternative embodiment, at least one side of the mitt or glove is quilted via means known in the art in any desirable pattern in order to reduce slippage between the plies in a multi-ply face and/or to form the thumbpocket.

In an alternative embodiment, an active material such as, for example, a bar of cleansing soap, may be inserted into the open end of the mitt or glove, then optionally that open end may be releasably secured via any of the above-mentioned securing methods capable of releasably securing, e.g. hook and loops.

In an alternative embodiment wherein the device is a washcloth, such devices have preferably at least 2-ply sheets and more preferably at least 3-ply sheets, with the latter being either 3 separate substrate sheets secured together or at least 1 substrate sheet folded upon itself with additional sheets attached thereto. The washcloths are secured around the periphery via any of the aforementioned securing techniques, with heat sealing being preferred. The washcloth may be quilted along its face to reduce slippage of its substrate sheets. As described above, the softness of each face of the washcloth may be controlled by the size of textured variation and the direction of the protuberances.

An alternative embodiment of the present invention is directed to the combination of the textured film device and an active material. The term "active material," as used herein is not intended merely to include detergent-active materials but also to include any substance capable of delivery via an article according to the present invention to give a benefit.

Examples of suitable active materials include known cleansers; i.e. surfactants and soaps; conditioners; moisturizers; bubble bath compositions; shaving foams; skin treatment agents such as sunscreens; tanning agents; anti-acne agents; anti-aging, i.e. wrinkles, fine lines, and other manifestations of photodamage, agents; anti-irritant agents; perfumes/fragrances and the like. The active materials may be in any suitable form such as a powder, a gel, a sol, a solid block, a semi-solid, a liquid, or any combination thereof.

Examples of suitable cleansers and conditioners include those disclosed in U.S. Pat. No. 5,804,539. Cleansers having low irritation properties such as shampoos available from Johnson & Johnson Consumer Companies, Inc., under the tradename, "Johnson's Baby Shampoo," and washes available from Johnson & Johnson Consumer Companies, Inc., under the tradename, "Johnson's Baby Bath," are preferred.

Examples of suitable sunscreens nonexclusively include butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, padimate o, red petrolatum, and mixtures thereof.

Examples of suitable tanning agents include dihydroxyacetone.

Examples of suitable anti-acne agents include, but are not limited to topical retinoids (tretinoin, isotretinoin, motretinide, adapalene, tazarotene, azelaic acid, retinol); salicylic acid; benzoyl peroxide; resorcinol; antibiotics such as tetracycline and isomers thereof, erythromycin, and the anti-inflammatory agents such as ibuprofen, naproxen, hetprofen; botanical extracts such as alnus, arnica, artemisia capillaris, asiasarum root, birth, calendula, chamomile, cnidium, comfrey, fennel, galla rhois, hawthrone, houttuynia, hypericum, jujube, kiwi, licorice, magnolia, olive, peppermint, philodendron, salvia, sasa albomarginata; imidazoles such as ketoconazole and elubiol, and those described in Gollnick, H et al. 196(I) Dermatology Sebaceous Glands, Acne and Related Disorders, 119–157 (1998), which is incorporated by reference herein, and mixtures thereof.

Preferred anti-acne agents include benzoyl peroxide, retinol, elubiol, antibiotics, and salicylic acid, with retinol and tretinoin being most preferred.

Examples of suitable anti-aging, i.e. wrinkles, fine lines, and other manifestations of photodamage, agents include, but are not limited to inorganic sunscreens such as titanium art dioxide and zinc oxide; organic sunscreens such as octyl-methyl cinnamates and derivatives thereof; retinoids; vitamins such as vitamin E, vitamin A, vitamin C, vitamin B, and derivatives thereof such as vitamin E acetate, vitamin C palmitate, and the like; antioxidants including beta carotene, alpha hydroxy acid such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrrolactic acid, alpha-hydroxyisovaleric acid, ethyl pyruvate, galacturonic acid, glucopehtonic acid, glurcopheptono 1,4-lactone, gluconic acid, gluconolactone, glucuronic acid, glucurronolactone, glycolic acid, isopropyl pyruvate, methyl pyruvate, mucic acid, pyruvia acid, saccharic acid, saccaric acid 1,4-lactone, tartaric acid, and tartronic acid; beta hydroxy acids such as beta-hydroxybutyric acid, beta-phenyl-lactic acid, beta-phenylpyruvic acid; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, safflower, and mixtures thereof.

Preferred anti-aging agents include retinoids, antioxidants, alpha-hydroxy acids and beta-hydroxy acid with retinol and tretinoin being most preferred.

Examples of suitable anti-irritant agents include colloidal oatmeal, oat extract, agents known for reducing the symptoms of diaper rash such as dimethicone, white petrolatum, zinc oxide, and mixtures thereof and the like.

The textured film device and the active material may be packaged together as in a system or kit. The kit preferably contains the desired liquid cleanser and/or other active material, in its own container. Alternatively, the active material may be substantially dry and impregnated into or deposited onto the film as disclosed in, for example, U.S. Pat. No. 5,980,931. In yet another embodiment, the active material may be placed in at least one enclosure attached, either fixedly or removably, to the textured film, the securing means, and/or the holding means. In a preferred embodiment, the enclosure is attached to the textured film and, for the spherical textured film device 10, located in the center 30 of the device 10.

In embodiments wherein the enclosure is attached to the device, the enclosure may be comprised of any material capable of enabling the transport of the primary agent from within the enclosure to outside of the enclosure at a desired time. Preferably, the enclosure has walls comprised of either a water soluble material or a water insoluble material.

Examples of suitable water soluble materials include, for example, water soluble films such as polyvinyl alcohol, cellulose derivatives such as methylcellulose, hydroxyethylcellulose, carboxymethylcellulose, gelatin, and those disclosed in Davidson, Robert L., et al., "Water Soluble Resins," Chapters 2–9 (1968). The thickness of the water soluble film may range from about 0.01 mm to about 0.8 mm, and preferably from about 0.025 mm to about 0.05 mm. The active material may be dispensed from the enclosure having walls comprised of water soluble materials by wetting the device with a sufficient amount of water needed to solubilize the walls.

Alternatively, the enclosure may possess walls comprised of a water insoluble film including, but not limited to polyvinyl chloride, polyvinylidine chloride, polyethylene, polypropylene, vinyl chloride copolymers, ethylene vinyl alcohol, and mixtures thereof. The thickness of the water insoluble film may range from about 0.01 mm to about 0.8 mm, and preferably from about 0.025 mm to about 0.05 mm.

The active material may be dispensed therefrom by applying pressure to the enclosure in order to puncture the water insoluble film membrane. Alternatively, the enclosure may be a container comprised of water insoluble material, wherein the walls of the container have a general thickness of from about 0.025 mm mm to about 3 mm, preferably from about 0.25 mm to about 1 mm. Such containers may be replaceable or refillable. The active material may be dispensed from such containers through at least one capped and/or valved dispensing hole in at least one wall of the container. Upon removal of the cap, the active material may be dispensed from the container. The valve, which may be activated by squeezing the walls of the container or by manually deflecting a member of the valve, may be in the form of a slitted membrane, ball and spring, duckbill, or any other valve known in the art of dispensing containers. See, e.g., U.S. Pat. Nos. 4,728,006, 4,782,975, 5,632,420, 5,680,969, 5,079,013, and French Patent No. 1,364,891.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLE 1
Comparison of Open Area

From a 20 cm×30 cm piece of each type of material described in Table B, three 3.8 cm by 3.8 cm samples of each material were scanned using a Hewlett Packard ScanJet IIC Scanner. These samples were oriented with the protuberances toward the scanner glass. The scans were made at 600 dpi (dots per inch) using a Sharp Black and White Photo setting and automatic brightness contrast control. The images were saved as "tiff" format for analysis using Image Pro Plus 3.0 image analysis software.

For each material set forth in Table B, the three images obtained from the three samples therefrom were imported into Image Pro Plus 3.0 software, then analyzed using a calibration corresponding to the scan of 600 dpi. The protuberance openings of each image were measured, then the area of each opening was calculated by the software. All of the opening areas for each sample were summed, then the open area was calculated by the equation: % Open Area= (Sum of areas of openings in image/Area of image)×100. The Open Area for each material is shown in Table B below:

TALBE B

| Materials for Open Area Analysis | |
|---|---|
| Type of Material | Open Area (%) |
| Perforated film (fine**) | 6.1 |
| Perforated film (large-elongated shape) | 13.4 |
| Perforated film (large-round shape) | 14.0 |
| Perforated film (intermediate) | 4.2 |
| Netted Mesh* | 69.1 |

*available from the San Francisco Soap Company
**The terms, "fine," "intermediate" and "large" refer to the number of textured variations/cm$^2$ in the film in decreasing order.

We observed that the cross-sectional shapes of the perforated films were film-like in appearance. By contrast, the netted mesh had individual strands of filaments having a cross-sectional shape that ranged from nearly round to kidney-shaped. The cross-sectional view of the netted mesh sections at locations where the strands were joined together appeared to have a "dog-bone" or "dumbbell"-like shape.

This Example illustrated that the perforated films of the present invention have a significantly lower open area relative to that of the netted mesh typically used in commercial puff cleansing devices. This Example further showed that the perforated films were distinct from the netted mesh in overall structure.

EXAMPLE 2
Manufacture and Use of the Perforated Film Device

A 20 cm×200 cm sheet of the film available from Tredegar Film Products, Inc. under the tradename, "VISPORE®" and having an open area of about 14% was folded back and forth upon itself in accordance with the method illustrated in FIG. 13 in order to form a corrugated structure having a height of about 3 cm. After tying the structure in the center with a conventional rubber band, a round, almost spherical implement resulted.

After depositing about 5 grams of a shower gel available from the Neutrogena Corporation under the tradename, "Rain Bath," onto the structure, the structure was used in a general cleansing fashion in a shower. This procedure was followed by three independent consumers.

It was found that the structure produced a significant amount of aesthetically-pleasing lather and effectively and gently cleaned the skin without irritation. Moreover, the users remarked that the structure was soft and non-irritating to the skin.

This Example showed that the novel structure containing a known shower gel was capable of producing a significant amount of lather without irritating the skin.

EXAMPLE 3
Lather Comparison—Diamond Mesh Puff Versus Perforated Film Device

Five devices, which were comprised of the film described in Example 2 were produced in accordance with the procedure set forth in Example 2. A second set of five devices were similarly made, but using a similar film having a 4.2% open area.

These devices were wetted for about 15 seconds with tap water having a temperature of 35° C., and the water was then allowed to drain therefrom for about 5 to 10 seconds. The structures were then shaken 3 times. Simultaneously therewith, the forearms of 5 subjects were wetted for about 15 seconds with similar water.

After applying 2 ml of a shower bath available from Johnson & Johnson Ltd. under the tradename, "pH 5.5 Body Wash" to each respective wetted forearm, each subject then independently rubbed a device of this example along the forearm to create a lather for about 30 seconds. Each respective device was then squeezed, and the lather produced therein was collected in an independent graduated cylinder in order to measure the foam volume.

This lathering process was repeated with a commercial diamond made puff available from the Body Shop. The results of this Example are shown below in Table D.

TABLE D

Foam Volume of Lather Produced by a Variety of Puffs

| Type of Puff | Foam Volume (ml) of User No.: 1 | Foam Volume (ml) of User No.: 2 | Foam Volume (ml) of User No.: 3 | Foam Volume (ml) of User No.: 4 | Foam Volume (ml) of User No.: 5 | Foam Volume (ml) Mean of 5 Users | Foam Volume (ml) Std. Dev. Of 5 Users |
|---|---|---|---|---|---|---|---|
| Film of Example 2 | 650 | 650 | 650 | 600 | 600 | 630 | 27 |
| Film of Example 3 | 450 | 600 | 450 | 450 | 400 | 470 | 42 |
| Body Shop Puff | 450 | 250 | 350 | 450 | 400 | 380 | 83 |

This Example showed that foam volume and quality were not sacrificed by the soft gentle cleansing offered by the puff of the present invention. Moreover, this Example showed that more lather is produced by perforated film puffs having a larger open area relative to those having a relatively smaller open area. In addition, this Example also showed that perforated film puffs, which have a lower overall open area than that of diamond mesh puffs, produced a significantly larger amount of lather relative to the diamond mesh puffs.

We claim:

1. A device comprising:
   a. at least one gathered piece of three-dimensional textured film having textured variations; and
   b. securing means for substantially permanently holding the at least one gathered piece of textured film together; wherein said textured film has an open area of no more than about 45%, based upon the total area of the textured film.

2. The device of claim 1 wherein the film is comprised of a polymer selected from the group consisting of polyethylene, polypropylene, ethylene vinyl acetate copolymer, metallocene polyethylene, and blends and copolymers thereof.

3. The device of claim 1 wherein the film has textured variations selected from the group consisting of holes, embossments, and combinations thereof.

4. The device of claim 3 wherein the embossments have a depth of about greater than about 0 mm to about 3 mm.

5. The device of claim 1 wherein the film contains textured variations in the amount of from about 1.6 textured variations/cm$^2$ to about 248 textured variations/cm$^2$.

6. The device of claim 1 wherein the film contains textured variations in the amount of from about 80 textured variations/cm$^2$ to about 200 textured variations/cm$^2$.

7. The device of claim 1 wherein the film contains textured variations in the amount of from about 5.0 textured variations/cm$^2$ to about 15 textured variations/cm$^2$.

8. The device of claim 1 wherein the film contains textured variations in the approximate shape of a circle, honeycomb, oval, heart, pear, hexagon, square, triangle, pentagon, stellate, rectangle or combination thereof.

9. The device of claim 1 wherein the textured film has an open area of greater than about 15% and less than about 35% based upon the total area of the perforated film.

10. The device of claim 1 further comprising an inner substrate that is substantially covered by the piece of textured film.

11. The device of claim 10 further comprising a second sheet of textured film, wherein the inner substrate is disposed between the two outer sheets of textured film.

12. The device of claim 10 wherein the inner substrate is a non-sheetlike, three-dimensional body.

13. The device of claim 1 further comprising a holding means.

14. The device of claim 1 wherein the device has a substantially spherical shape.

15. The use of the device of claim 1 as a personal cleansing product.

16. The method of making the device of claim 1 comprising:
   a) gathering at least one piece of textured film to produce a desired arrangement of film; and
   b) securing the at least one piece of textured film with a securing means.

17. The method of claim 16 wherein the at least one piece of textured film is C-folded prior to gathering.

18. A device comprising:
   at least one piece of three-dimensional textured film, wherein the device is in the form of a spherical poof, a mitt, a cloth having at least about 1.3 textured variations/cm$^2$, a glove, a plurality of textured film appendages attached to a holding means or a textured film pad attached to a holding means; wherein said textured film has an open area of no more than about 45%, based upon the total area of the textured film.

19. The device of claim 18 in the form of the mitt, the cloth, or the glove, having a first side and a second side, wherein at least one of the sides is comprised of a three-dimensional textured film.

20. The device of claim 19 wherein at least the first side has protuberances facing outward.

21. The device of claim 19 wherein the first side and the second side comprise three-dimensional textured films having open areas and the open area of the three-dimensional textured film on the first side is different from the open area of the textured film on the second side.

22. The device of claim 19 wherein at least one side is quilted.

23. A system comprised of:
   a) the device of claim 18; and
   b) an active material.

24. The system of claim 23 wherein the active material is selected from the group consisting of moisturizers, bubble bath compositions, cleansers; conditioners; sunscreens; shaving foams; tanning agents; anti-acne agents; anti-aging agents; anti-irritant agents; perfumes/fragrances; moisturizers and mixtures thereof.

25. The system of claim 24 wherein the active material is selected from the group consisting of oatmeal, perfumes/fragrances, cleansers, conditioners and mixtures thereof.

26. The use of the system of claim 23 as a personal cleansing product.

27. The system of claim 23 wherein the active material is impregnated into and/or deposited onto the textured film.

28. The system of claim 23 further comprising an enclosure, wherein the active material is inside the enclosure.

29. The system of claim 28 wherein the enclosure has walls comprised of water soluble material or water insoluble material.

30. The system of claim 29 wherein the water soluble material is selected from the group consisting of methylcellulose, hydroxyethylcellulose, caroxymethylcellulose, gelatin, and mixtures thereof.

31. The system of claim 29 wherein the water insoluble material is selected from the group consisting of polyvinyl chloride, polyvinylidine chloride, polyethylene, polypropylene, ethylene vinyl alcohol, and mixtures and copolymers thereof.

32. The system of claim 29 wherein the water insoluble material is dispensed from a valved aperture in the enclosure.

33. The system of claim 28 wherein the enclosure is refillable or replaceable.

34. A method of cleaning the skin comprised of
   a) applying a cleanser to the skin and/or to the device of claim 18; and
   b) using the device to create a lather.

35. A method of cleaning the skin comprised of using the device of claim 18 containing a cleanser to create a lather on the skin.

36. A method for treating acne comprised of
   a) applying an anti-acne agent to the skin and/or to the device of claim 18; and
   b) using the device to distribute the anti-acne agent.

37. The method of claim 36 wherein the anti-acne agent is selected from the group consisting of benzoyl peroxide, retinol, elubiol, antibiotics, salicylic acid, and mixtures thereof.

38. A method for reducing skin irritation comprising:
   a) applying an anti-irritant agent to the skin and/or to the device of claim 18; and
   b) using the device to distribute the anti-irritant agent.

39. The method of claim 38 wherein the anti-irritant agent is selected from the group consisting of oatmeal, dimethicone, white petrolatum, zinc oxide, and combinations thereof.

40. A method for promoting healthy skin comprising:
   a) applying an active material to the skin and/or to the device of claim 18; and
   b) using the device to distribute the active material.

* * * * *